United States Patent
Avery

(10) Patent No.: US 11,229,585 B2
(45) Date of Patent: Jan. 25, 2022

(54) HAIR CONDITIONING COMPOSITION

(71) Applicant: Conopco, Inc., Englewood Cliffs, NJ (US)

(72) Inventor: Andrew Richard Avery, Ellesmere Port (GB)

(73) Assignee: Conopeo, Inc., Englewood Cliffs, NJ (US)

(*) Notice: Subject to any disclaimer, the term of this patent is extended or adjusted under 35 U.S.C. 154(b) by 0 days.

(21) Appl. No.: 16/759,507

(22) PCT Filed: Oct. 24, 2018

(86) PCT No.: PCT/EP2018/079164
§ 371 (c)(1),
(2) Date: Apr. 27, 2020

(87) PCT Pub. No.: WO2019/086311
PCT Pub. Date: May 9, 2019

(65) Prior Publication Data
US 2020/0330337 A1 Oct. 22, 2020

(30) Foreign Application Priority Data
Oct. 30, 2017 (EP) .................................... 17199284

(51) Int. Cl.
A61K 8/04 (2006.01)
A61K 8/06 (2006.01)
A61K 8/31 (2006.01)
A61K 8/34 (2006.01)
A61K 8/41 (2006.01)
A61K 8/891 (2006.01)
A61Q 5/12 (2006.01)

(52) U.S. Cl.
CPC ............. A61K 8/042 (2013.01); A61K 8/062 (2013.01); A61K 8/31 (2013.01); A61K 8/342 (2013.01); A61K 8/416 (2013.01); A61K 8/891 (2013.01); A61Q 5/12 (2013.01); A61K 2800/596 (2013.01)

(58) Field of Classification Search
CPC ......... A61K 8/042; A61K 8/062; A61K 8/31; A61K 8/342; A61K 8/416; A61K 8/891; A61K 2800/596; A61Q 5/12
See application file for complete search history.

(56) References Cited

U.S. PATENT DOCUMENTS

| 2006/0122989 | A1* | 2/2006 | Wells |
| 2006/0083704 | A1 | 4/2006 | Torgerson |
| 2006/0293410 | A1 | 12/2006 | Tokita et al. |
| 2012/0022210 | A1 | 1/2012 | Davio et al. |
| 2012/0093757 | A1 | 4/2012 | Murray et al. |

FOREIGN PATENT DOCUMENTS

| WO | WO9631188 | 10/1996 |
| WO | WO2015122989 | 8/2015 |
| WO | WO2016041748 | 3/2016 |
| WO | WO2016123675 | 8/2016 |

OTHER PUBLICATIONS

Search Report and Written Opinion in EP17199284; dated Jan. 4, 2018.
Search Report and Written Opinion in PCTEP2018079164; dated Dec. 19, 2018.
WO for PCTEP2018079164; dated Sep. 19, 2019.
IPRP2 in PCTEP2018079164; dated Dec. 10, 2019.
Anonymous; Anonymous: "Nonlinear Polymers"; Polymer Science Learning Center; Sep. 10, 2019; 5.

* cited by examiner

Primary Examiner — Alma Pipic
(74) Attorney, Agent, or Firm — Edward A. Squillante, Jr.

(57) ABSTRACT

A hair care composition obtainable by blending a conditioning gel phase with an aqueous emulsion of a non-linear organopolysiloxane comprising monomer units of silsesquioxane having a formula $(RSiO_{3/2})_n$ where n=1, R is an alkyl group, preferably methyl, ethyl or propyl, and copolymer segments of polydialkylsiloxane; the conditioning gel phase being formed from a cationic surfactant, a high melting point (25° C. or higher) fatty compound and an aqueous carrier; and the aqueous emulsion of the non-linear organopolysiloxane having an aqueous continuous phase consisting of water and a blend of non-ionic and cationic surfactants and a dispersed phase consisting of the non-linear organopolysiloxane and a hydrocarbon oil, wherein the weight ratio of the non-linear organopolysiloxane to the hydrocarbon oil is 40:60 to 65:35. Alternatively, the aqueous continuous phase consists of water and a cationic surfactant.

20 Claims, No Drawings

HAIR CONDITIONING COMPOSITION

CROSS REFERENCE TO RELATED APPLICATION

This application is a U.S. National Stage Application under 35 U.S.C. § 371 of International Application No. PCT/EP2018/079164, filed on Oct. 24, 2018, which claims the benefit of European Application No. 17199284.5, filed on Oct. 30, 2017, the entire disclosures of which are hereby incorporated by reference for any and all purposes.

FIELD OF THE INVENTION

This invention relates to hair care compositions containing a non-linear organopolysiloxane, "oil in water" emulsion.

BACKGROUND OF THE INVENTION

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. A variety of approaches have been developed to condition the hair. A common method of providing conditioning benefits to the hair is through the use of conditioning agents such as cationic surfactants and polymers, high melting point fatty compounds, low melting point oils, silicone compounds, and mixtures thereof.

Despite the prior art, there still exists the opportunity to increase the benefits delivered through conditioning hair care compositions. A particular need exists for hair care compositions which can deliver enhanced hair shaping benefits such as hair strand alignment, and manageability.

US 2012/093757 discloses a hair conditioner comprising a silicone and a conditioning gel phase, said gel phase obtainable by heating a fatty alcohol and an oil until they are molten, separately heating a cationic surfactant in water until it is dissolved/suspended, then adding the molten fatty alcohol and oil mix to the cationic surfactant before adding any remaining ingredients.

WO 2016/041748 discloses a hair care composition obtainable by blending a conditioning gel phase with an aqueous polydimethylsiloxane polymer emulsion; the conditioning gel phase being formed from a cationic surfactant, a high melting point (25° C. or higher) fatty compound and an aqueous carrier; and the aqueous polydimethylsiloxane polymer emulsion having an aqueous continuous phase consisting of water and a blend of non-ionic and cationic surfactants and a dispersed phase consisting of a polydimethylsiloxane polymer and a hydrocarbon oil, wherein the polydimethylsiloxane polymer has a dynamic viscosity of 50,000 to 1 10,000 cP at 25° C., and the hydrocarbon oil has a kinematic viscosity of 1 to 35 cSt at 40° C. and the specific gravity of 0.76 to 0.87 at 25° C., and the weight ratio of the polydimethylsiloxane polymer to the hydrocarbon oil is 45:55 to 70:30.

WO96/31188 discloses hair treatment compositions which can generate style benefits while giving good conditioning comprising a non-rigid emulsion polymerized cross-linked silicone conditioning polymer having from about 0.05% to 10% branched monomer units.

The present invention provides a conditioning composition with superior hair shaping capability and preferably, also increased deposition efficiency of a benefit agent onto chemically damaged hair.

SUMMARY OF THE INVENTION

Accordingly, in a first aspect, the present invention provides a hair care composition obtainable by blending a conditioning gel phase with an aqueous emulsion of a non-linear organopolysiloxane comprising monomer units of silsesquioxane having a formula $(RSiO_{3/2})_n$
where n=1,
R is an alkyl group, preferably methyl, ethyl or propyl, and copolymer segments of polydialkylsiloxane; the conditioning gel phase being formed from a cationic surfactant, a high melting point (25° C. or higher) fatty compound and an aqueous carrier; and the aqueous emulsion of the non-linear organopolysiloxane having an aqueous continuous phase consisting of water and a blend of non-ionic and cationic surfactants and a dispersed phase consisting of the non-linear organopolysiloxane and a hydrocarbon oil, wherein the weight ratio of the non-linear organopolysiloxane to the hydrocarbon oil is 40:60 to 65:35.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

Conditioning Gel Phase

Examples of suitable cationic surfactants which are useful for forming the conditioning gel phase include quaternary ammonium cationic surfactants corresponding to the following general formula:

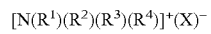

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Alternatively, primary, secondary or tertiary fatty amines may be used in combination with an acid to provide a cationic surfactant suitable for providing the conditioning gel phase suitable for use in the invention. The acid protonates the amine and forms an amine salt in situ in the hair care composition. The amine is therefore effectively a non-permanent quaternary ammonium or pseudo-quaternary ammonium cationic surfactant.

Suitable fatty amines of this type include amidoamines of the following general formula:

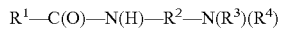

$$R^1\text{---}C(O)\text{---}N(H)\text{---}R^2\text{---}N(R^3)(R^4)$$

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms.

Specific examples of suitable materials of the above general formula are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

The acid used may be any organic or mineral acid which is capable of protonating the amine in the hair care composition. Suitable acids include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the hair care composition).

By "high melting point" in the context of this invention is generally meant a melting point of 25° C. or higher. Generally, the melting point ranges from 25° C. up to 90° C., preferably from 40° C. up to 70° C. and more preferably from 50° C. up to about 65° C.

The high melting point fatty compound can be used as a single compound or as a blend or mixture of at least two high melting point fatty compounds. When a blend or mixture of fatty compounds is used, the melting point means the melting point of the blend or mixture.

Suitable fatty compounds of this type have the general formula R—X, wherein R is an aliphatic carbon chain and X is a functional group (e.g. alcohol or carboxylic acid or a derivative thereof such as ester or amide).

R is preferably a saturated aliphatic carbon chain comprising from 8 to 30 carbon atoms, preferably from 14 to 30 carbon atoms, more preferably from 16 to 22 carbon atoms.

R can contain, in addition to carbon and hydrogen atoms, ether linkages, and other groups such as amino groups. Preferably R is a linear alkyl chain comprising from 8 to 30 carbon atoms, preferably from 14 to 30 carbon atoms, more preferably from 16 to 22 carbon atoms.

X is preferably an —OH group.

Most preferably, the fatty compound is a fatty alcohol of general formula $CH_3(CH_2)_n$ OH, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty compounds may also be suitable.

The level of fatty compound suitably ranges from 0.01 to 10 wt %, preferably from 0.1 to 8 wt %, more preferably from 0.2 to 7 wt % and most preferably from 0.3 to 6 wt % (by total weight of fatty compound based on the total weight of the hair care composition).

The weight ratio of cationic surfactant to fatty compound is suitably from 1:1 to 1:10, preferably from 1:1.5 to 1:8, optimally from 1:2 to 1:5.

Conditioning gel phases suitable for use in the invention may be characterized as gel ($L_β$) surfactant mesophases consisting of surfactant bilayers.

In a general process for the preparation of such conditioning gel phases, the cationic surfactant, high melting point fatty compound and aqueous carrier are heated to form a mixture, which is cooled under shear to room temperature. The mixture undergoes a number of phase transitions during cooling, normally resulting in a gel ($L_β$) surfactant mesophase consisting of surfactant bilayers. The bilayers may grow, swell or fold to form extended sheets or spherical vesicles.

Preferably, the formation of the gel ($L_β$) surfactant mesophase is controlled by maintaining the temperature of the mixture so that it falls within a specified range, generally from about 55 to about 67° C., in the mixing vessel.

In an example of such a preferred process, the fatty compound and the cationic surfactant may be "comelted" in a first vessel to form an isotropic phase. The comelt will typically comprise from 45 to 90 wt % fatty alcohol of general formula $CH_3(CH_2)_n OH$, where n is an integer from 7 to 29, preferably from 15 to 21; from 10 to 40 wt % cationic surfactant of general formula $[N(R^1)(CH_3)_3]^+(X)^-$, where $R^1$ is a $C_{16}$ to $C_{22}$ saturated alkyl chain and X is halide; and from 0 to 15 wt % water (by weight based on the total weight of the comelt). The comelt in the first vessel is typically maintained at a temperature sufficient to maintain the fatty compound in a liquid phase (usually around 80 to 85° C.). The comelt is then added to a second vessel containing water at about 50 to about 60° C., and the comelt and the water are mixed. In the second vessel, the temperature of the mixture of the comelt and the water is controlled such that it is maintained at from 56 to 65° C., preferably from 58 to 62° C., more preferably around 60° C. The cationic surfactant component of the comelt as described above may also comprise or consist of a fatty amidoamine of general formula:

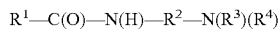
$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms. In this case the water in the second vessel will suitably include from 0.01 to 3 wt % of an organic or mineral acid which is capable of protonating the fatty amidoamine.

In an alternative example of a preferred process, a 'comelt' (such as described above) and water may be independently added to a mixing vessel and mixed in a continuous process in which the temperature of the mixture of comelt and water is controlled by modifying the temperature of water added to the mixture. Water may be added in a single dose or in aliquots. Typically, a first water vessel is maintained at around 40° C. and is pumped into the mixing vessel while a second water vessel is maintained at a sufficient temperature to modify the temperature of the mixture of water with comelt such that it falls within the required range as specified above.

In another example of a preferred process, the fatty compound and the cationic surfactant may be combined in an aqueous dispersion. According to this process, an aqueous dispersion is prepared, which dispersion typically comprises from 25 to 50 wt % water, from 4 to 20 wt % fatty alcohol of general formula $CH_3(CH_2)_nOH$, where n is an integer from 7 to 29, preferably from 15 to 21; and from 1 to 5 wt % fatty amidoamine of general formula:

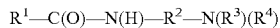
$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms (by weight based on the total weight of the dispersion). Preferably, the temperature of the aqueous dispersion is maintained above the melting temperature of the fatty alcohol, preferably at least 5° C. higher than the melting point of the fatty alcohol. A cationic surfactant of general formula $[N(R^1)(CH_3)_3]^+(X)^-$, where $R^1$ is a $C_{16}$ to $C_{22}$ saturated alkyl chain and X is halide; may then be added and mixed into the aqueous dispersion, generally at a level of from 0.5 to 5 wt % (by weight based on the total weight of the mixture).

Preferably the mixing of the cationic surfactant with the aqueous dispersion is monitored by measurement of viscosity, such that when the viscosity change plateaus, mixing is complete (generally after about 20 to 60 minutes of mixing). After mixing is complete, the fatty amidoamine is neutralised with a suitable acid as described above. Preferably, the temperature of the mixture of the aqueous dispersion and the cationic surfactant is maintained at from 56 to 67° C., preferably from 58 to 65° C., more preferably around 63° C. Preferably, the process is a batch process.

Another preferred process for making a conditioning gel phase suitable for use in the invention comprises forming an aqueous isotropic solution of cationic surfactant (typically of general formula $[N(R^1)(CH_3)_3]^+(X)^-$, where $R^1$ is a $C_{16}$ to $C_{22}$ saturated alkyl chain and X is halide); and mixing the aqueous isotropic solution of cationic surfactant with molten fatty compound (typically a fatty alcohol of general formula $CH_3(CH_2)_nOH$, where n is an integer from 7 to 29, preferably from 15 to 21). Typically, the fatty alcohol is maintained at a temperature sufficient to maintain it in a liquid phase (usually around 80 to 85° C.), prior to its addition to the aqueous isotropic solution of cationic surfactant. Preferably, the temperature of the mixture of the fatty alcohol and aqueous isotropic solution is maintained at from 55° C. to 65° C., more preferably at from 58° C. to 62° C. and most preferably at about 60° C.

Aqueous Non-Linear Organopolysiloxane Emulsion

The hair care composition of the invention is obtainable by blending a conditioning gel phase (as described above) with a non-linear organopolysiloxane emulsion having an aqueous continuous phase consisting of water and a blend of nonionic and cationic surfactants and an internal, dispersed phase consisting of the non-linear organopolysiloxane and an oil, wherein the weight ratio of the organopolysiloxane to the oil is 40:60 to 65:35, preferably 50:50 to 65:35, more preferably 55:45 to 65:35, most preferably 60:40.

The oil may be a synthetic oil, such as a hydrocarbon derived oil. Preferably the oil is a hydrocarbon oil.

The non-linear organopolysiloxane of the present invention comprises monomer units of silsesquioxane having a formula $(RSiO_{3/2})_n$ where n=1;

R is an alkyl group, preferably methyl, ethyl or propyl, more preferably methyl;

and copolymer segments of polydialkylsiloxane, wherein the alkyl groups are preferably methyl, and the end groups are preferably —OH; the most preferred polydialkylsiloxane is dimethiconol.

The weight average molecular weight of the organopolysiloxanes of the present invention is preferably greater than 700,000 Da, more preferably greater than 800,000 Da, still more preferably greater than 900,000 Da, even more preferably greater than 950,000 Da, most preferably greater than 1,000,000 Da but typically less than 1,400,000 Da, preferably less than 1,200,000 Da measured using gel permeation chromatography. For the avoidance of doubt, the unit Dalton (Da) is also known as unified atomic mass unit (u).

A stress-controlled rheometer MCR 501 (Anton Paar, Austria) fitted with parallel geometry was used to characterise the organopolysiloxane/hydrocarbon blends. The tests were performed at temperature 20° C. with gap size 0.5 mm across a frequency window from 100 Hz to 0.1 Hz, at a fixed strain 0.5%. Excess samples at the plate edge were trimmed. After loading, samples were left for 60 seconds for stress relaxation. The data were collected in logarithmic steps with 10 points per decade. The storage modulus of the dispersed phase comprising the non-linear organopolysiloxane and a hydrocarbon oil is sensitive to the weight ratio of organopolysiloxane to oil and for the weight ratios specified above, may range at 10 Hz, from $1\times10^2$ Pa to $2\times10^3$ Pa.

The rheology of the organopolysiloxane was also characterised, following evaporation of the hydrocarbon. For these measurements mass was tracked over time, while the hydrocarbon evaporated. Once the mass indicated that no hydrocarbon remained, the organopolysiloxane sample was characterised as above.

Preferably, the non-linear organopolysiloxane has a storage modulus measured at 10 Hz, ranging from $2\times10^3$ Pa to $3\times10^4$ Pa, preferably from $8\times10^3$ Pa to $2\times10^4$ Pa, more preferably from $1\times10^4$ Pa to $1.6\times10^4$ Pa.

WO2015/122989 and US2012/022210, the contents of which are hereby incorporated by reference describe methods for preparing the non-linear organopolysiloxane and the aqueous emulsion of the organopolysiloxane of the present invention.

Without wishing to be bound by theory, it is believed that at a molecular level, multiple classes of topological structure will result from a polycondensation reaction between a linear precursor molecule comprising on average two functional groups, with branching agents containing more than two reactive groups per molecule. For this reason, the organopolysiloxane of the present invention is described as a non-linear organopolsiloxane to define the product of such reactions in WO2015/122989 and US2012/022210. Such reaction product may comprise more than one of the classes of topological polymer structure well known in the art. Such structures include for example; branched, hyperbranched, cyclic, multicyclic and combinations of these.

Suitable hydrocarbon oils in the context of the present invention include saturated, non-polar straight or branched-chain aliphatic or alicyclic hydrocarbons having from about 10 to about 50 carbon atoms, and mixtures thereof.
Preferred hydrocarbon oils in the context of the present invention are light mineral oil and isohexadecane.

Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons, in which the number of carbon atoms per hydrocarbon molecule generally ranges from $C_{10}$ to $C_{40}$.

The mineral oil may be characterised in terms of its viscosity, where light mineral oil is less viscous than heavy mineral oil. A suitable light mineral oil will generally have a kinematic viscosity of 3.9 to 5.0 cSt at 40° C. and a specific gravity of 0.810 to 0.830 at 25° C. Such materials are commercially available under the brand name Lytol™.

Isohexadecane, such as that supplied under the trade name Permethyl 101A for example, available from Presperse Inc., N.J., U.S.A. is a branched hydrocarbon of molecular formula C16H34 suitable for use in the present invention. It is a colourless liquid with a boiling point around 240 C.

The aqueous emulsion for use in the invention has an aqueous continuous phase comprising a blend of a nonionic surfactant such as an alkyl polyethytlene glycol ether, for example PEG-7 propylheptyl ether and a cationic surfactant such as cetyltrimethylammonium chloride.

The total amount of surfactant used will vary depending on the particular surfactant selected and the target composition of the emulsion, but generally ranges from 0.84 to 2.51% by weight of the aqueous emulsion. The internal, dispersed phase comprising the organopolysiloxane and the hydrocarbon within the aqueous emulsion may range from 50% to 73% by weight of the emulsion.

Other surfactant choices typically applied when emulsifying silicone can also be applied to the components of the internal dispersed phase of the invention described above, without adversely affecting performance, since this performance is derived from the action of the deposited internal phase upon the hair. For example, the use of a cationic emulsifying surfactant alone, without any nonionic emulsifying surfactant can also be considered.

The % by weight of the conditioner formulation represented by the internal, dispersed phase of the emulsion may range from 0.05 to 3.5%, preferably 0.1 to 3%, more preferably 0.2 to 2.75% and even more preferably from 0.5 to 2.5%.

Product Form and Optional Ingredients

The hair care compositions of the invention are primarily intended for topical application to the hair and/or scalp of a human subject in order to improve hair properties such as hair fibre lubrication, smoothness, softness, manageability, alignment, bodification, shaping power and shine.

The hair care compositions of the invention are typically "rinse-off" compositions to be applied to the hair and then, in part, rinsed away.

A particularly preferred product form is a conditioner for the treatment of hair (typically after shampooing) and subsequent rinsing.

Generally, such a composition is applied to the hair (preferably hair which has been shampooed and then rinsed with water), and then worked through the hair. Preferably the composition is then left to penetrate the hair for a period of about one to three minutes before rinsing it from the hair with water. Typically, from about 1 g to about 50 g of the composition is applied to the hair or scalp.

The hair care compositions of the invention will generally comprise from about 20% to about 95% of water, preferably at least 30%, more preferably at least 40%, still more preferably at least 50%, even more preferably at least 60% or even at least 70%, but typically not more than 94%, preferably not more than 93%, more preferably not more than 92%, still more preferably not more than 91%, even more preferably not more than 90% or even not more than 80% by weight based on total weight. Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The hair care compositions of the invention may also incorporate other optional ingredients to enhance performance and/or consumer acceptability. Suitable optional ingredients include, but are not limited to: preservatives, colouring agents, chelating agents, antioxidants, fragrances, antimicrobials, antidandruff agents, cationic conditioning polymers, styling ingredients, sunscreens, proteins and hydrolysed proteins.

The invention will now be further described by reference to the following Examples. In the Examples, all percentages are by weight based on total weight, unless otherwise specified.

EXAMPLES

Example 1: Effect of Invention Emulsions Upon Shaping Benefits

Hair conditioning compositions were prepared, having ingredients as shown in table 1 below. Conditioner Examples 1, 2, 3, 4 and 5 represent compositions according to the invention.

In table 1, Example emulsions 1, 2, 3, 4 and 5 represent aqueous organopolysiloxane emulsions according to the invention. The dispersed phase of example emulsion 1 contains an internal phase with the non-linear organopolysiloxane to oil ratio of 65:35. The dispersed phase of example emulsion 2 contains an internal phase with the non-linear organopolysiloxane to oil ratio of 55:45. The dispersed phase of example emulsion 3 contains an internal phase with the non-linear organopolysiloxane to oil ratio of 50:50. The dispersed phase of example emulsion 4 contains an internal phase with the non-linear organopolysiloxane to oil ratio of 40:60. The dispersed phase of example emulsion 5 contains an internal phase with the non-linear organopolysiloxane to oil ratio of 60:40.

To evaluate the performance of these products on hair, the hair was first shampoo'd with the formulation in Table A before applying the example conditioner to the wet, rinsed hair.

TABLE A

| Ingredients | % Active | Total Active in Formulation (% w/w) |
|---|---|---|
| Sodium Laureth Sulfate | 70 | 20 |
| Cocoamidopropyl Betaine | 30 | 5.33 |
| Glycol Distearate, ammonium Laureth Sulfate, Ammonium Lauryl Sulfate, Ammonium Xylenesulfonate, Cocamide MEA | 20 | 6.5 |
| DMDM Hydantoin | 50 | 0.4 |
| Colorant CL42090 | 100 | 0.000028 |
| Colorant CL19140 | 100 | 0.001 |
| Parfum | 100 | 0.4 |
| Sodium Chloride | 100 | As needed |
| Aqua | 100 | To 100 |

Treatment with Pantene Pro-V Volume and Body shampoo & conditioner was used as the comparative example, for comparison with the inventive example conditioner products. These comparative products were acquired in the U.K. The shampoo bore batch code 7164484700 B10 and the conditioner bore batch code 60154847A0 A10.

TABLE 1

| Ingredient INCI name | % Active | Conditioner Ex 1 % w/w | Conditioner Ex 2 % w/w | Conditioner Ex 3 % w/w | Conditioner Ex 4 % w/w | Conditioner Ex 5 % w/w |
|---|---|---|---|---|---|---|
| Aqua | 100 | 91.965 | 91.965 | 91.965 | 91.965 | 91.965 |
| Lactic Acid | 88 | 0.325 | 0.325 | 0.325 | 0.325 | 0.325 |
| Cetearyl Alcohol | 100 | 4 | 4 | 4 | 4 | 4 |
| C16-C18, Behentrimonium Chloride and dipropylene glycol | 70 | 1 | 1 | 1 | 1 | 1 |
| Stearamidopropyl dimethylamine | 100 | 1 | 1 | 1 | 1 | 1 |
| Disodium EDTA | 100 | 0.05 | 0.05 | 0.05 | 0.05 | 0.05 |
| Potassium Chloride | 100 | 0.1 | 0.1 | 0.1 | 0.1 | 0.1 |
| Ex Emulsion 1 | 50 | 1 | 0 | 0 | 0 | 0 |
| Ex Emulsion 2 | 50 | 0 | 1 | 0 | 0 | 0 |
| Ex Emulsion 3 | 50 | 0 | 0 | 1 | 0 | 0 |
| Ex Emulsion 4 | 50 | 0 | 0 | 0 | 1 | 0 |
| Ex Emulsion 5 | 50 | 0 | 0 | 0 | 0 | 1 |
| Methyl chloroisothaizolinone Methylisothiazolinone | 1.50 | 0.06 | 0.06 | 0.06 | 0.06 | 0.06 |
| Parfum | 100 | 0.5 | 0.5 | 0.5 | 0.5 | 0.5 |

Evaluation

The conditioner compositions of Ex 1 to 5 and the Comparative example were evaluated as follows:

Hairstyle shape evaluation method on Dry Hair

Mannequin heads implanted with dark brown European hair, which had been cut to a single length, in this case chin length, were shampoo'd, conditioned and blow styled. Half head testing of conditioner formulations was performed by parting the hair down the middle and applying test formulations to either side of the head. 4 g of shampoo was applied to each half of the head, massaged through the hair and rinsed out, then 4 g of conditioner was applied to each half head, massaged through the hair and rinsed out, before blow styling.

A hairdryer, on medium heat and full power settings and a round brush were used to create a bobbed hairstyle. For the testing described here, a Parlux Hairtools 3200 hairdryer and a Ceramic Plus Ion brush such as available from Olivia Garden (U.S.) were used.

After blow styling was complete, the shape of the style achieved was evaluated by analyzing a photograph taken facing the front of the mannequin head. For the purpose of acquiring photographic images, both camera and mannequin head were located at fixed positions within an enclosed cabinet, under fixed temperature (20° C.), relative humidity (50%) and lighting conditions. A vertical line was drawn through the image passing through a fixed point on the mannequin head, around the centre of the forehead. A horizontal line was plotted through the lowest point of the hairstyle for each half of the head. The distance along the vertical line from the fixed point, to its intersection with the horizontal line was recorded.

This process was repeated for multiple styling events per formulation and the data averaged and reported as mean distance in the table below. Formulations demonstrating smaller mean distance values deliver styles for which the lowest observed point of the styled hair was consistently nearer the top of the head.

Result

TABLE 2

| Example | Non-linear organopolysiloxane to oil ratio | Mean distance (mm) | Std dev | 95% confidence interval |
|---|---|---|---|---|
| Conditioner Ex 1 | 65:35 | 223.5 | 2.1 | 2.0 |
| Conditioner Ex 2 | 55:45 | 218.0 | 2.0 | 2.8 |
| Conditioner Ex 3 | 50:50 | 219.7 | 7.0 | 8.0 |
| Conditioner Ex 4 | 40:60 | 222.0 | 0.0 | n/a |
| Conditioner Ex 5 | 60:40 | 206.3 | 2.1 | 2.0 |
| Comparative Example | N/A | 238.1 | 8.3 | 8.2 |

A low value of mean distance is desirable as it indicates that the hairstyle holds its shape well and does not drop out under gravity.

All example formulations therefore showed more desired shaping performance vs the comparative example.

Furthermore, it can be noted that compositions with the organopolysiloxane to oil ratio of 50:50 to 60:40 show the best styling benefits.

Hair conditioning compositions characterised by emulsions where the dispersed phase has a higher non-linear organopolysiloxane to oil ratio, such as 70:30 or higher are not practical to formulate with, because at such ratios the rheology of the ingredient makes it more challenging to emulsify.

Example 2: Effect of the Emulsions of WO2016/041748 on Shaping Benefits

Comparative hair conditioning compositions were prepared using the emulsions of WO2016/041748, having ingredients as shown in table 3 below. Comparative Examples A, B and C represent comparative compositions comprising the silicone emulsion of WO2016/041748.

In table 3, Comparative emulsions A, B and C represent aqueous polydimethylsiloxane emulsions according to WO2016/041748. The dispersed phase of comparative emulsion A contains an internal phase with the polydimethylsiloxane to oil ratio of 60:40. The dispersed phase of comparative emulsion B contains an internal phase with the polydimethylsiloxane to oil ratio of 50:50. The dispersed phase of comparative emulsion C contains an internal phase with the polydimethylsiloxane to oil ratio of 40:60.

To evaluate the performance of these products on hair, the hair was first shampoo'd with the formulation in Table A of Example 1 before applying the example conditioner to the wet, rinsed hair.

TABLE 3

| Ingredient | | Comparative | Comparative | Comparative |
| --- | --- | --- | --- | --- |
| INCI name | % Active | Ex A % w/w | Ex B % w/w | Ex C % w/w |
| Aqua | 100 | 91.965 | 91.965 | 91.965 |
| Lactic Acid | 88 | 0.325 | 0.325 | 0.325 |
| Cetearyl Alcohol | 100 | 4 | 4 | 4 |
| C16-C18, Behentrimonium Chloride and dipropylene glycol | 70 | 1 | 1 | 1 |
| Stearamidopropyl dimethylamine | 100 | 1 | 1 | 1 |
| Disodium EDTA | 100 | 0.05 | 0.05 | 0.05 |
| Potassium Chloride | 100 | 0.1 | 0.1 | 0.1 |
| Comparative Emulsion 1 | 50 | 1 | 0 | 0 |
| Comparative Emulsion 2 | 50 | 0 | 1 | 0 |
| Comparative Emulsion 3 | 50 | 0 | 0 | 1 |
| Methylchloroisothaizolinone Methylisothiazolinone | 1.50 | 0.06 | 0.06 | 0.06 |
| Parfum | 100 | 0.5 | 0.5 | 0.5 |

Evaluation

The comparative compositions Comp Ex A to C were evaluated using the same method of evaluation used in Example 1.

Result

TABLE 4

| Example | Non-linear organopolysiloxane to oil ratio | Mean distance (mm) | Std dev | 95% confidence interval |
| --- | --- | --- | --- | --- |
| Comparative Ex A | 60:40 | 236.8 | 6.9 | 6.8 |
| Comparative Ex B | 50:50 | 229.4 | 1.2 | 1.4 |
| Comparative Ex C | 40:60 | 233.0 | 1.8 | 1.7 |

A low value of mean distance is desirable as it indicates that the hairstyle holds its shape well and does not drop out under gravity.

Example formulations 5, 3 and 4 of table 1 can be compared with comparative Examples A, B and C respectively. In all 3 comparisons, it can be noted that the examples of the present invention showed more desired shaping performance when compared to the comparative examples.

The invention claimed is:

1. A hair care composition obtained by blending a conditioning gel phase with an aqueous emulsion of a non-linear organopolysiloxane comprising monomer units of silsesquioxane having a formula $(RSiO_{3/2})_n$ where n=1, and R is an alkyl group, and copolymer segments of polydialkylsiloxane; the conditioning gel phase being formed from a cationic surfactant, a 25° C. or higher melting point fatty compound and an aqueous carrier; and wherein the aqueous emulsion of the non-linear organopolysiloxane has an aqueous continuous phase consisting of water and a blend of non-ionic and cationic surfactants, and a dispersed phase consisting of the non-linear organopolysiloxane and a hydrocarbon oil, wherein the weight ratio of the non-linear organopolysiloxane to the hydrocarbon oil is 40:60 to 65:35, the hair care composition conditions hair after shampooing and further wherein the non-linear organosiloxane and hydrocarbon oil make up from 0.05 to 3.5% by weight of the hair care composition, the cationic surfactant to fatty compound present at a weight ratio from 1:1 to 1:10 and the fatty compound makes up from 0.01 to 10% by weight of the hair care composition.

2. The hair care composition according to claim 1, wherein the weight ratio of the non-linear organopolysiloxane to the hydrocarbon oil is 50:50 to 60:40.

3. The hair care composition according to claim 1, wherein the weight ratio of the non-linear organopolysiloxane to the hydrocarbon oil is 60:40.

4. The hair care composition according to claim 1, wherein the non-linear organopolysiloxane has a storage modulus of $2\times10^3$ Pa to $3\times10^4$ Pa measured at 10 Hz, using a stress-controlled rheometer MCR 501 (Anton Paar, Austria) fitted with parallel geometry performed at 20° C. with gap size 0.5 mm across a frequency window from 100 Hz to 0.1 Hz and at a fixed strain of 0.5%.

5. The hair care composition according to claim 1, wherein the hydrocarbon oil is isohexadecane or mineral oil.

6. The hair care composition according to claim 1, in which the cationic surfactant used to form the conditioning gel phase is selected from etyltrimethylammonium chloride (CTAC), behenyltrimethylammonium chloride (BTAC), protonated stearamidopropyldimethylamine, and mixtures thereof.

7. The hair care composition according to claim 1, in which the fatty compound used to form the conditioning gel phase is selected from cetyl alcohol, stearyl alcohol and mixtures thereof.

8. The hair care composition according to claim 1, in which the conditioning gel phase is a gel ($L_\beta$) surfactant mesophase obtained by a process comprising the steps of heating the cationic surfactant, fatty compound and aqueous carrier to form a mixture and controlling the formation of the gel ($L_\beta$) surfactant mesophase by maintaining the temperature of the mixture so that it falls within a range of from 55 to 67° C.

9. A hair care composition obtained by blending a conditioning gel phase with an aqueous emulsion of a non-linear organopolysiloxane comprising monomer units of silsesquioxane having a formula $(RSiO_{3/2})_n$
where n=1, and
R is an alkyl group, and copolymer segments of polydialkylsiloxane; the conditioning gel phase being formed from a cationic surfactant, a 25° C. or higher melting point fatty compound and an aqueous carrier; and wherein the aqueous emulsion of the non-linear organopolysiloxane has an aqueous continuous phase consisting of water and a cationic surfactant, and a dispersed phase consisting of the non-linear organopolysiloxane and a hydrocarbon oil, wherein the weight ratio of the non-linear organopolysiloxane to the hydrocarbon oil is 40:60 to 65:35, the hair care composition conditions hair after shampooing and further wherein the non-linear organosiloxane and hydrocarbon oil make up from 0.05 to 3.5% by weight of the hair care composition, the cationic surfactant to fatty compound present at a weight ratio from 1:1 to 1:10 and the fatty compound makes up from 0.01 to 10% by weight of the hair care composition.

10. The hair care composition of claim 1, wherein R is methyl, ethyl, or propyl.

11. The hair care composition of claim 9, wherein R is methyl, ethyl, or propyl.

12. The hair care composition according to claim 9, wherein the weight ratio of the nonlinear organopolysiloxane to the hydrocarbon oil is 50:50 to 60:40.

13. The hair care composition according to claim 9, wherein the weight ratio of the nonlinear organopolysiloxane to the hydrocarbon oil is 60:40.

14. The hair care composition according to claim 9, wherein the non-linear organopolysiloxane has a storage modulus of $2\times10^3$ Pa to $3\times10^4$ Pa measured at 10 Hz, using a stress-controlled rheometer MCR 501 (Anton Paar, Austria) fitted with parallel geometry performed at 20° C. with gap size 0.5 mm across a frequency window from 100 Hz to 0.1 Hz and at a fixed strain of 0.5%.

15. The hair care composition according to claim 9, wherein the hydrocarbon oil is isohexadecane or mineral oil.

16. The hair care composition according to claim 9, in which the cationic surfactant used to form the conditioning gel phase is selected from cetyltrimethylammonium chloride (CTAC), behenyltrimethylammonium chloride (BTAC), protonated stearamidopropyldimethylamine, and mixtures thereof.

17. The hair care composition according to claim 9, in which the fatty compound used to form the conditioning gel phase is selected from cetyl alcohol, stearyl alcohol and mixtures thereof.

18. The hair care composition according to claim 9, in which the conditioning gel phase is a gel ($L_\beta$) surfactant mesophase obtained by a process comprising the steps of heating the cationic surfactant, fatty compound and aqueous carrier to form a mixture and controlling the formation of the gel ($L_\beta$) surfactant mesophase by maintaining the temperature of the mixture so that it falls within a range of from 55 to 67° C.

19. The hair care composition of claim 1, wherein the level of cationic surfactant is present at a total weight that ranges from 0.1 to 10 wt %, based on the total weight of the hair care composition.

20. The hair care composition of claim 9, wherein the level of cationic surfactant is present at a total weight that ranges from 0.1 to 10 wt %, based on the total weight of the hair care composition.

* * * * *